(12) United States Patent
Agrawal et al.

(10) Patent No.: US 11,896,447 B2
(45) Date of Patent: Feb. 13, 2024

(54) SAFEGUARDS AGAINST SEPARATION FROM PORTABLE MEDICINE DELIVERY DEVICES

(71) Applicant: Medtronic MiniMed, Inc., Northridge, CA (US)

(72) Inventors: Pratik J. Agrawal, Stevenson Ranch, CA (US); Jack D. Pryor, Ladera Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 157 days.

(21) Appl. No.: 17/693,584

(22) Filed: Mar. 14, 2022

(65) Prior Publication Data

US 2023/0285112 A1    Sep. 14, 2023

(51) Int. Cl.
*A61B 90/98* (2016.01)
*A61B 5/145* (2006.01)

(52) U.S. Cl.
CPC .......... *A61B 90/98* (2016.02); *A61B 5/14532* (2013.01); *A61M 2205/3584* (2013.01)

(58) Field of Classification Search
None
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | VanAntwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |

(Continued)

*Primary Examiner* — Carlos Garcia
(74) *Attorney, Agent, or Firm* — Carter, DeLuca & Farrell LLP

(57) ABSTRACT

Disclosed herein are techniques related to safeguards against separation from portable medicine delivery devices. In some embodiments, the techniques may involve monitoring a wireless connection established between a portable computing device and a portable medicine delivery device. The techniques may also involve making a determination, based on the result of the monitoring, that the portable medicine delivery device is outside a predetermined range of the portable computing device. The techniques may further involve generating a notification based on the determination. The notification may be indicative of a user of the portable computing device being unaccompanied by the portable medicine delivery device.

20 Claims, 3 Drawing Sheets

(56) References Cited

U.S. PATENT DOCUMENTS

| | | |
|---|---|---|
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Nunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,672,328 B2 | 6/2017 | Saint et al. |
| 10,391,270 B2 * | 8/2019 | Adams ................ A61M 15/009 |
| 10,661,007 B2 * | 5/2020 | Estes ................ A61M 5/14244 |
| 10,786,206 B1 * | 9/2020 | Miller ................ A61B 5/7221 |
| 10,835,727 B2 | 11/2020 | Montalvo et al. |
| 2003/0212311 A1 * | 11/2003 | Nova ................ A61N 1/37258 |
| | | 600/300 |
| 2007/0123819 A1 | 5/2007 | Mernoe et al. |
| 2010/0160861 A1 | 6/2010 | Causey, III et al. |
| 2013/0157571 A1 * | 6/2013 | Wondka ............ H04W 52/0245 |
| | | 455/41.2 |
| 2019/0240414 A1 * | 8/2019 | Sjöstedt ................ G16H 40/40 |
| 2020/0206427 A1 * | 7/2020 | Sjöstedt ................ H04W 4/029 |
| 2020/0327973 A1 | 10/2020 | Pryor et al. |
| 2021/0236731 A1 * | 8/2021 | Mazlish ................ A61M 5/1723 |
| 2021/0322678 A1 * | 10/2021 | Evelyn ................ A61M 5/2033 |

\* cited by examiner

SAFEGUARDS AGAINST SEPARATION FROM PORTABLE MEDICINE DELIVERY DEVICES

FIELD

The present disclosure relates to portable medicine delivery and, more particularly, to safeguards against separation from portable medicine delivery devices.

BACKGROUND

Diabetes mellitus ("diabetes") is a metabolic disease that affects the regulation of glucose by insulin. Diabetes affects hundreds of millions of people and is among the leading causes of death globally. Diabetes has been categorized into three types: type 1, type 2, and gestational diabetes. Type 1 diabetes is associated with the body's failure to produce insulin. Type 2 diabetes is associated with the body's failure to produce sufficient amounts of insulin. Gestational diabetes is associated with insulin-blocking hormones that are produced during pregnancy. Gestational diabetes often resolves after pregnancy; however, in some cases, gestational diabetes develops into type 2 diabetes.

Treatment for various diseases and medical conditions, such as diabetes, typically involves administering doses of medicine. When administering a liquid medicine by injection, for example, an appropriate dosage may be set in a medicine delivery device (e.g., a syringe, a medicine delivery pen, or a pump) and dispensed therefrom. Regardless of the particular delivery device utilized for administering medicine, some medicine administration systems assist users with medicine administration and tracking, thereby helping users manage their diseases and/or medical conditions.

SUMMARY

Disclosed herein are techniques related to safeguards against separation from portable medicine delivery devices. The techniques may be practiced using a processor-implemented method; a system (e.g., a portable computing device) including one or more processors and one or more processor-readable storage media; and/or one or more non-transitory processor-readable storage media.

In some embodiments, the techniques may involve monitoring a wireless connection established between a portable computing device and a portable medicine delivery device. The techniques may also involve making a determination, based on the result of the monitoring, that the portable medicine delivery device is outside a predetermined range of the portable computing device. The techniques may further involve generating a notification based on the determination. The notification may be indicative of a user of the portable computing device being unaccompanied by the portable medicine delivery device.

The details of one or more embodiments of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

A detailed description of embodiments of the disclosure will be made with reference to the accompanying drawings, wherein like numerals designate corresponding parts in the figures.

DETAILED DESCRIPTION

Figure 1:
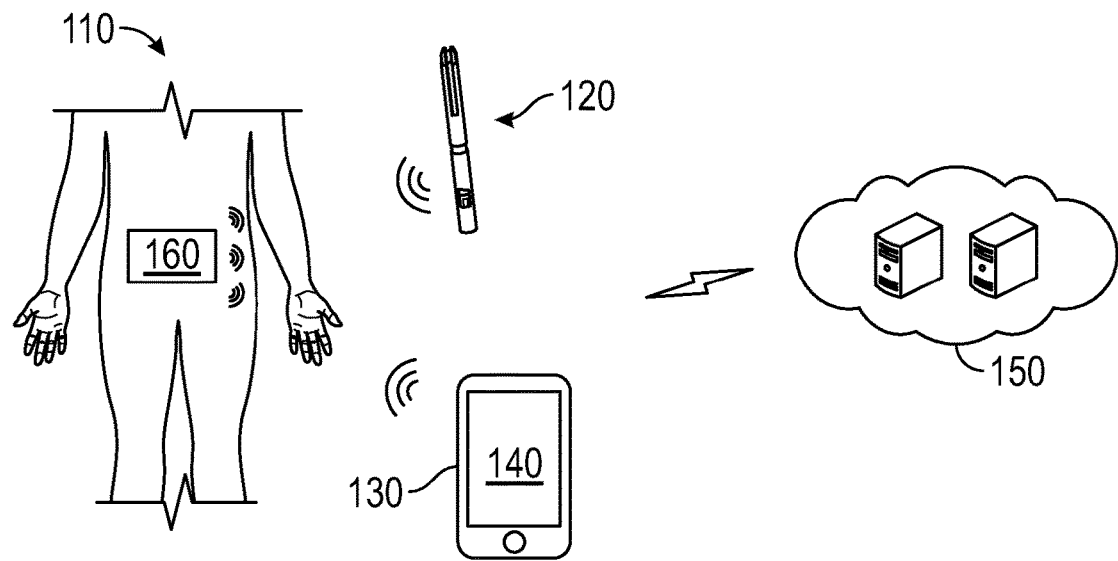
FIG. 1 is a diagram of an example system including a portable medicine delivery device, in accordance with aspects of the present disclosure.

A portable medicine delivery device according to the present disclosure may be any medicine delivery device that a person can carry from place to place, such as an insulin pen, an albuterol inhaler, or an epinephrine injector, among other things. A portable medicine delivery device may be used to provide medicine to a person regularly and/or on-demand. Accordingly, tracking of a portable medicine delivery device helps ensure that the medicine is readily available to the person. If tracking reveals that a portable medicine delivery device has been left behind and is not available, information can be provided to help retrieve the portable medicine delivery device, or recommendations can be provided to a user to manage a health condition without the portable medicine delivery device. For convenience, the disclosure below may use a portable insulin delivery device, such as an insulin pen, as an example, but it is intended and will be understood that any description relating to a portable insulin delivery device shall be applicable to any portable medicine delivery device and to any system that includes a portable medicine delivery device FIG. 1 is a diagram of an example system 110, in accordance with aspects of the present disclosure. The illustrated system 110 includes a portable medicine delivery device 120, a portable computing device 130, a data processing system 150, and a sensor device 160. The portable medicine delivery device 120 may be any device that delivers medicine to a person and that may be carried by the person from place to place.

The portable medicine delivery device 120 is in wireless communication with the portable computing device 130, which may be a smartphone, a tablet, a smartwatch, a laptop, or another type of computing device that can be carried by a person from place to place (e.g., a mobile computing device that accompanies a person from place to place such that the mobile computing device can serve as a proxy for the person in terms of location and other data). In FIG. 1, the portable computing device 130 is illustrated as a smartphone to provide an example, but it may be any suitable portable computing device (e.g., a dedicated device for displaying health-related data, generating health-related recommendations, and/or controlling one or more other devices). The portable computing device 130 can execute a health management application 140, which will be described in more detail later herein. For now, it is sufficient to note that the health management application 140 may use components of the portable computing device 130 to determine whether the portable medicine delivery device 120 is within communication range of the portable computing device 130. Based on the determination, the health management application 140 may manage various aspects of dosing of the medicine and/or activities of a person, among other things.

In various embodiments, the portable medicine delivery device 120 may be an injection pen. For example, device 120 may be a reusable injection pen configured to removably receive a medicine cartridge, e.g., a cartridge of insulin. As another example, device 120 may be a disposable injection pen that is discarded when its medicinal contents (e.g., insulin stored in a reservoir) are depleted. In either example, device 120 may be configured to inject a selected dose of medicine into a person and record information concerning the injected dose of medicine, such as a dose amount and/or timestamp data associated with the dose. In various embodiments, the portable medicine delivery device 120 may be a prescription medical device. The present disclosure may describe the portable medicine delivery device 120 in connection with diabetes management, but it is intended and understood that the portable medicine delivery device 120 may be applied to manage other diseases and/or medical conditions. The portable medicine delivery device 120 will be described in greater detail in connection with FIG. 2. Such and other embodiments are contemplated to be within the scope of the present disclosure.

In aspects of the present disclosure, the portable computing device 130 may be communicatively paired with the portable medicine delivery device 120, such as via Bluetooth pairing, Wi-Fi pairing, and/or another type of communication pairing. In aspects, the pairing of the portable computing device 130 with the portable medicine delivery device 120 may unlock certain features of the health management application 140 executing on the portable computing device 130

In aspects of the present disclosure, the health management application 140 of the portable computing device 130 can monitor and/or control features, functionalities, and/or operations of the portable medicine delivery device 120. For example, the health management application 140 may include one or more sets of instructions corresponding to a dose calculator and/or decision support instructions that can cause calculation of dose recommendations (e.g., a recommended dose of medicine for the user to administer using the portable medicine delivery device 120), among other things. The health management application 140 may implement a user interface on the hardware of the portable computing device 130 to allow a user to visualize and/or manage health-related data. For example, the health management application 140 may be configured to control some functionalities of the portable medicine delivery device 120 and/or to provide an interactive user interface to allow a user to manage settings of the portable medicine delivery device 120.

The portable computing device 130 can additionally, or alternatively, be used to obtain, process, and/or display data related to the health condition of the user, including the condition for which the portable medicine delivery device 120 is used to treat. In various embodiments, the portable computing device 130 may be operable to track the location of the user, physical activity of the user (such as step count; movement distance, velocity, and/or acceleration; estimated calories burned; and/or activity duration), and/or interactions of the user with the portable computing device 130. In aspects, the health management application 140 can aggregate and process the data to generate decision support outputs, e.g., therapy recommendations.

With continuing reference to FIG. 1, the system 110 includes a data processing system 150. In various embodiments, the data processing system 150 may include one or more computing devices arranged in a computer system and/or interconnected via a communication network, e.g., including servers and/or databases in the cloud. Persons skilled in the art will recognize such and other data processing systems 150 and will understand how to implement them (e.g., as centralized or distributed systems).

In the illustrative embodiment of FIG. 1, the system 110 includes a sensor device 160 that monitors one or more physiological conditions of a person. Examples of physiological conditions monitored by sensor device 160 include analyte levels (e.g., glucose concentration levels), heart rate, blood pressure, user activity, and temperature, among other things. In various embodiments, the sensor device 160 may be a wearable sensor device such as a continuous glucose monitor (CGM) that obtains interstitial glucose measurements that are processed to produce sensed glucose values. A CGM can include suitable electronics (e.g., a processor, a memory, a transceiver, and/or a battery or other suitable power source) for processing, storing, and/or transmitting glucose values for the user. In various embodiments, such glucose values can be utilized by the health management application 140, for example, to display glucose data and/or generate dose recommendations, among other things. In various embodiments, the glucose values can be utilized by the portable medicine delivery device 120 to calculate and/or provide dose recommendations (e.g., a recommended dose of medicine for the user to administer using the portable medicine delivery device 120). Such embodiments are merely provided as examples, and variations are contemplated to be within the scope of the present disclosure.

For the avoidance of doubt, the aspects and embodiments shown or described in connection with FIG. 1 are merely provided as examples, and variations are contemplated to be within the scope of the present disclosure. For example, in various embodiments, the system 110 may not include a sensor device 160. In various embodiments, the system 110 may support and/or provide services for non-portable medicine delivery devices in addition to providing support and/or services for portable medicine delivery devices. Such and other variations are contemplated to be within the scope of the present disclosure.

Figure 2:
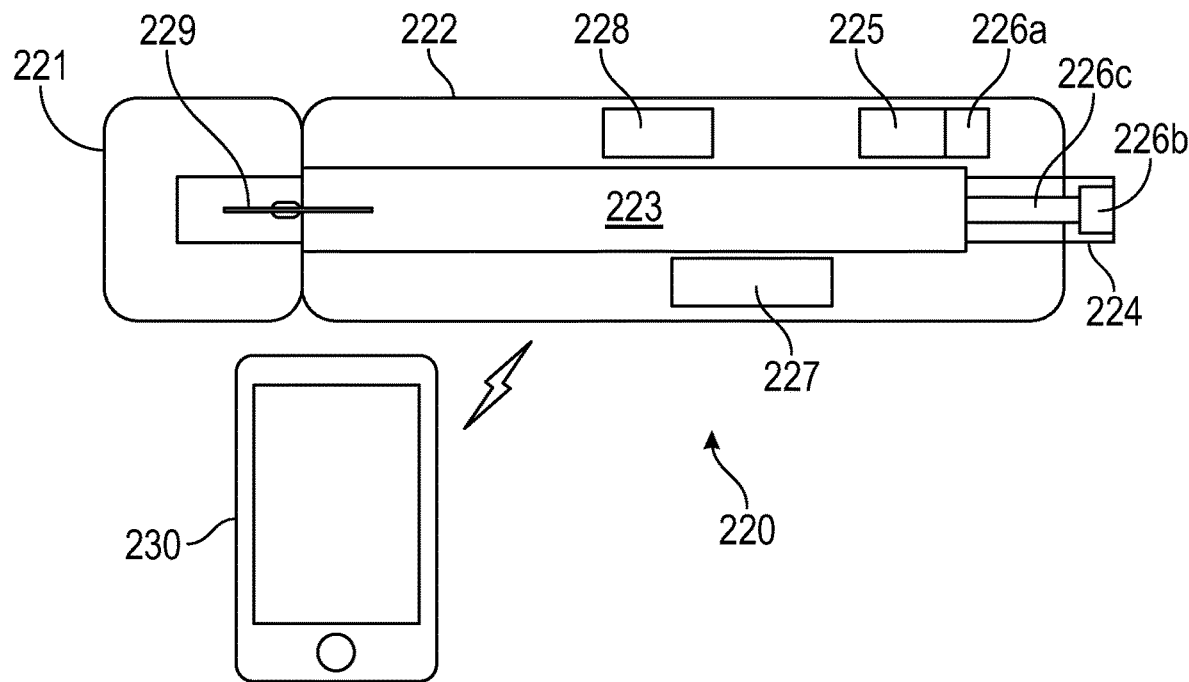
FIG. 2 is a block diagram of an example medicine injection pen and associated computing device, in accordance with aspects of the present disclosure.

Referring now to FIG. 2, an example portable medicine delivery device 220 and example components thereof are shown using a block diagram. FIG. 2 also shows a portable computing device 230 that can communicatively connect with or pair with the portable medicine delivery device 220. In various embodiments, the portable medicine delivery device 220 may have the form factor of a medicine "pen," such as the form factor of an insulin pen, among other things. The portable medicine delivery device 120 of FIG. 1 may be implemented as the portable medicine delivery device 220 of FIG. 2.

The illustrated portable medicine delivery device 220 includes a cap 221 configured to protect a medicine dispensing element (e.g., a needle 229) and includes a housing 222 configured to contain a replaceable medicine cartridge 223, e.g., an insulin cartridge. The portable medicine delivery device 220 further includes a dose dispensing mechanism 224 to dispense medicine contained in medicine cartridge 223 out of portable medicine delivery device 220 (e.g., through needle 229); a dose setting mechanism 225 to enable the selection and/or setting of a dose of medicine to be dispensed; an operations monitoring mechanism 228 (e.g., including one or more switches, sensors (electrical, optical, acoustic, magnetic, etc.), encoders, etc.) to determine that the portable medicine delivery device 220 is being operated and/or to monitor the operation of the portable medicine delivery device 220 (e.g., to determine an amount of medicine set and/or dosed); and electronics 227 that can include a processor, a memory, a transceiver, an accelerometer, an antenna for geolocation, and/or a battery or other suitable power source, among other things. A transceiver of the electronics 227 may implement communications protocols such as those that will be described below in connection with communications electronics 335 of FIG. 3. Examples of such communications protocols include, without limitation, Bluetooth and Wi-Fi, among other things.

The following paragraphs describe operation of the portable medicine delivery device 220 by way of example. Variations are contemplated to be within the scope of the present disclosure.

Prior to dose administration, a user may set, e.g., dial, the amount of a dose using a dose knob 226a of dose setting mechanism 225. The amount of the dose may be adjusted up or down by rotating dose knob 226a in an appropriate direction, thereby arriving at a desired dose amount. Once the appropriate dosage has been set, the user may apply a force against a dose dispensing button 226b of dose dispensing mechanism 224 to actuate dose delivery. More specifically, the user may press against dose dispensing button 226b to thereby drive a driving element 226c, e.g., a drive screw, of dose dispensing mechanism 224 against an abutment, e.g., a piston, of medicine cartridge 223. This may cause an amount of medicine to be dispensed from cartridge 223 through needle 229 into the user in accordance with the dose amount set using dose setting mechanism 225.

Operations monitoring mechanism 228 may sense movement of a rotating and/or translating driving element 226c of dose dispensing mechanism 224. Operations monitoring mechanism 228 may include one or more switches, sensors, and/or encoders for this purpose. Any suitable switch(es), sensor(s), and/or encoder(s) may be utilized to sense rotary and/or linear movement. Non-limiting examples of such include rotary and linear encoders, Hall effect and other magnetic-based sensors, linearly variable displacement transducers, optical sensors, etc. With respect to an encoder, for example, the encoder can be configured to sense the rotation of driving element 226c, which also translates to dispense medicine; thus, by sensing rotation of driving element 226c, the translational movement of driving element 226c can be readily determined. Movement of the encoder may be represented as data, and electronics 227 may include a processor configured to determine the amount of medicine dosed based on this data.

In aspects, electronics 227 may include a memory device configured to store the amount of a dose along with a timestamp for that dose and/or any other information associated with the dose.

In aspects, electronics 227 may include a transceiver configured to transmit the amount of the dose and related information to a portable computing device 230. In such aspects, any transmitted information may be marked as transmitted, and any information that is not transmitted due to a connection failure may be queued for transmission upon subsequent establishment of a connection.

Dose dispensing mechanism 224 can be a manually powered mechanism, a motorized mechanism, or an assisted mechanism (e.g., a mechanism that operates partly on manual power and partly on motorized power). Regardless of the particular configuration of the dose dispensing mechanism 224, when a force (e.g., a manual force, electrically powered motor force, or combinations thereof) is applied to driving element 226c of dose dispensing mechanism 224, driving element 226c may cause medicine to be displaced from medicine cartridge 223 according to a set or dialed amount. In aspects, dose dispensing mechanism 224 can be operated such that rotation and/or translation of the driving element, e.g., driving element 226c, is facilitated by a variable tension spring or a variable speed motor to inject the dose over a specific time frame (e.g., one second, five seconds, etc.).

As mentioned above, the aspects and embodiments shown and/or described in connection with FIG. 2 are merely provided as examples, and variations are contemplated to be within the scope of the present disclosure. For example, in various embodiments, a portable medicine delivery device may have a different form factor and/or may have different components, more components, or fewer components, than those shown in FIG. 2. Such and other variations are contemplated to be within the scope of the present disclosure.

Figure 3:
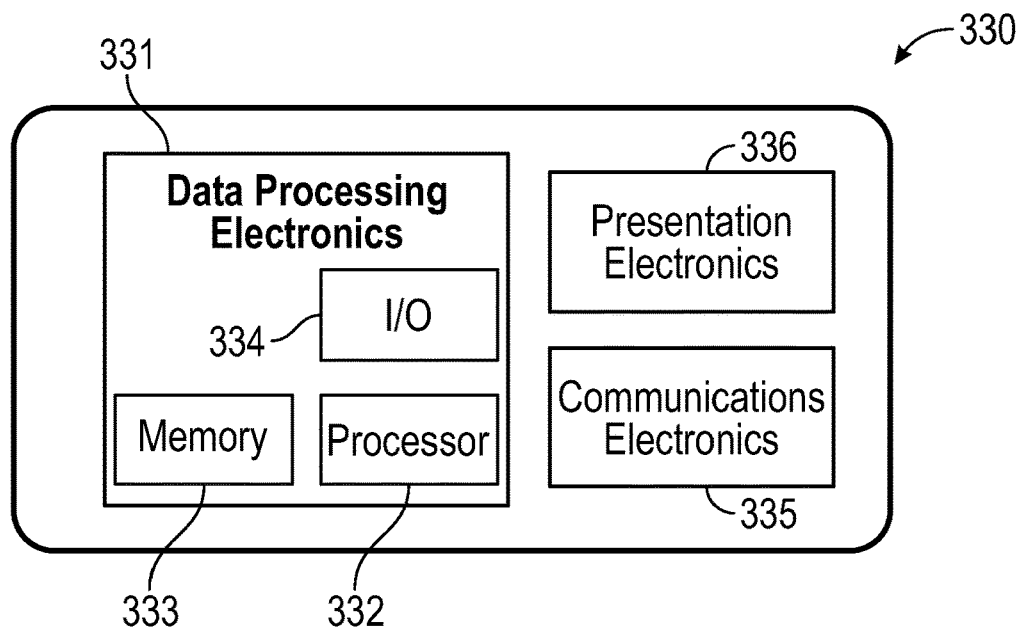
FIG. 3 is a block diagram of example components of a computing device, in accordance with aspects of the present disclosure.

Referring now to FIG. 3, example components of a portable computing device 330 are shown using a block diagram. The illustrated portable computing device 330 includes data processing electronics 331, communications electronics 335, and presentation electronics 336. The portable computing device 130 of FIG. 1 may be implemented as the portable computing device 330 of FIG. 3. In various embodiments, the portable computing device 330 may be a smartphone, a tablet, a smartwatch, a laptop, or another type of computing device that can be carried by a person from place to place.

The data processing electronics 331 includes a processor 332 that processes data, a memory 333 in communication with the processor 332 to store data, and input/output (I/O) electronics 334 that interface with other components, electronics, and/or devices and/or with a user of the portable computing device 330. The processor 332 can include a central processing unit (CPU), a microcontroller, an application specific integrated circuit (ASIC), a graphics processing unit (GPU), and/or other types of processing circuitry, or various combinations of the foregoing.

The memory 333 can store processor-executable code or instructions which, when executed by the processor 332, configures the data processing electronics 331 to perform various operations, e.g., such as receiving, processing, and/or transmitting commands and/or data. In aspects, the data processing electronics 331 can cause transmission of raw or processed data to a data processing system (e.g., 150, FIG. 1). To support various functions of the data processing electronics 331, the memory 333 can store data, such as instructions, values, images, and other software elements processed or referenced by the processor 332. For example, various types of Random-Access Memory (RAM) devices, Read Only Memory (ROM) devices, Flash Memory devices, and other suitable storage media can be used to implement storage functions of the memory 333.

The I/O electronics 334 enables the data processing electronics 331 to interface with communications electronics 335 to utilize various types of wired or wireless interfaces or protocols (e.g., a wireless transmitter/receiver (Tx/Rx)) compatible with typical data communication standards to enable communication between the data processing electronics 331 and other devices or systems, such as the portable medicine delivery device (e.g., 120, FIG. 1) and/or Global Positioning System (GPS). Examples of data communication standards or protocols include, but are not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, other cellular communications, NFC (Near Field Communication), Wi-Fi, parallel interfaces, Ethernet, universal serial bus (USB), lightning, thunderbolt, and other wired interfaces, and the Global Positioning System, among others. The I/O electronics 334 of the data processing electronics 331 can also interface with other external interfaces, data storage devices, and/or visual or audio devices, etc. This may enable I/O electronics 334 to retrieve and transfer data that can be processed by the processor 332, stored in the memory 333, and/or exhibited on output electronics of the portable computing device 330 and/or an external device.

The presentation electronics 336 of the portable computing device 30 can be configured to be in data communication with the data processing electronics 331, e.g., via the I/O electronics 334, to provide a visual presentation, an audio presentation, and/or other sensory presentation for implementing the user interface of a health management application (e.g., 140, FIG. 1). In some examples, the presentation electronics 336 can include various types of displays, speakers, or printing interfaces, e.g., including, but not limited to, light-emitting diode (LED); liquid crystal display (LCD); audio signal transducer apparatuses; and/or toner, liquid inkjet, solid ink, dye sublimation, inkless (e.g., such as thermal or UV) printing apparatuses, etc.

The various components of device 330 enable health management application 140 to support health management decisions. For example, communications electronics 335 and data processing electronics 331 enable acquisition and storage of dose data and related information (e.g., time information; dose setting and/or dose dispensing information; and/or other information about a portable medicine delivery device 220 and/or the environment as it relates to a dosing event). In aspects, presentation electronics 336 and data processing electronics 331 enable implementation of a user interface for browsing a list of previous doses; viewing an estimate of medicine active in the patient's body (e.g., insulin-on-board); receiving user input indicative of carbohydrates consumed and/or medicine dosed; and/or calculating and recommending an appropriate dose of medicine.

The aspects and embodiments shown and/or described in connection with FIG. 3 are merely provided as examples, and variations are contemplated to be within the scope of the present disclosure. For example, in various embodiments, a portable computing device may include different components, more components, or fewer components, than those shown in FIG. 3 and may include different functionality, more functionality, or less functionality than described in connection with FIG. 3. In various embodiments, some or all of certain components may be part of various other components. For example, some or all of I/O electronics 334 may not be part of data processing electronics 331 and may be part of one or more other components. Such and other variations are contemplated to be within the scope of the present disclosure.

The disclosure above described aspects, embodiments, and examples of a system including a portable medicine delivery device. The following will describe how the system can be used to practice techniques related to safeguards against separation from portable medicine delivery devices. More specifically, such techniques may help avoid a situation in which a user leaves a particular location (e.g., the user's home or office) without the user's portable medicine delivery device. In some embodiments, the system may determine that such a situation will occur based on tracking whether a portable medicine delivery device (e.g., 120, FIG. 1) is within range of a portable computing device (e.g., 130, FIG. 1). As used herein, a portable medicine delivery device is "within range" of a portable computing device if a communication connection (or if a communication connection of a predetermined strength) is established between the portable medicine delivery device and the portable computing device. As used herein, a portable medicine delivery device is "outside range" (i.e., not within range) of a portable computing device if a communication connection (or if a communication connection of a predetermined strength) cannot be established between the portable medicine delivery device and the portable computing device.

As mentioned above, a portable medicine delivery device according to the present disclosure may be any medicine delivery device that a person can carry from place to place, such as an insulin pen, an albuterol inhaler, or an epinephrine injector, among other things. A portable medicine delivery device may be used to provide medicine to a person regularly and/or on-demand. Accordingly, tracking of a portable medicine delivery device helps ensure that the medicine is readily available to the person. If tracking reveals that a portable medicine delivery device has been left behind and is not available, information can be provided to help retrieve the portable medicine delivery device, or recommendations can be provided to a user to manage a health condition without the portable medicine delivery device. For convenience, the disclosure below will use a portable insulin delivery device, such as an insulin pen, as an example, but it is intended and will be understood that any description relating to a portable insulin delivery device shall be applicable to any portable medicine delivery device and to any system that includes a portable medicine delivery device.

As described above and referring to FIG. 1, a portable medicine delivery device 120 may have electronics (e.g., 227, FIG. 2) that include a transceiver. A portable computing device 130 may have communications electronics (e.g., 335, FIG. 3) that provide wired or wireless communication capability. In accordance with aspects of the present disclosure, a transceiver of a portable medicine delivery device 120 and communication electronics of a portable computing device 130 may communicate with each other to form a wired or wireless communication connection, such as a Bluetooth connection or a Wi-Fi connection, among others. In various embodiments, the establishment and maintenance of such a communication connection may be monitored by an application executing on the portable computing device 130, such as by the health management application 140 and/or by another application. As described below, monitoring the establishment and maintenance of such a communication connection enables determining whether a portable medicine delivery device 120 is within range.

Figure 4:
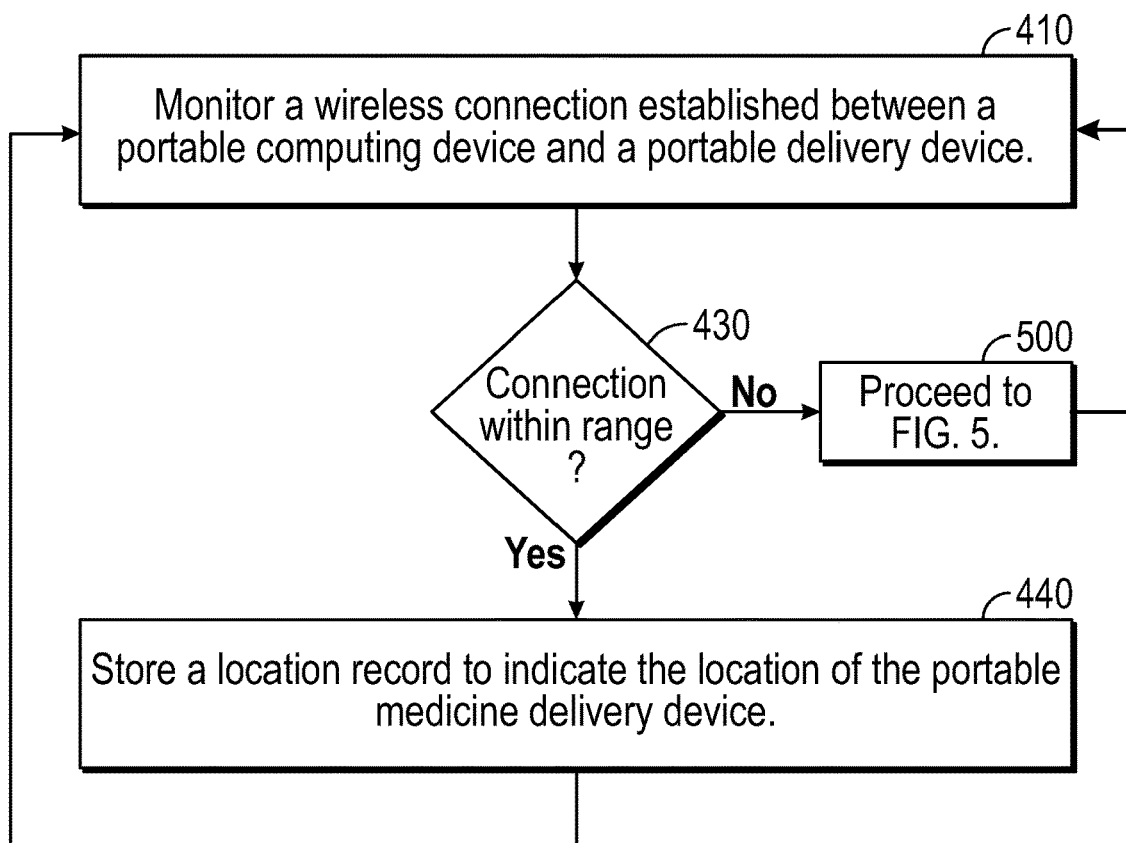
FIGS. 4-5 are flow diagrams depicting example techniques related to safeguards against separation from portable medicine delivery devices, in accordance with aspects of the present disclosure.
Figure 5:
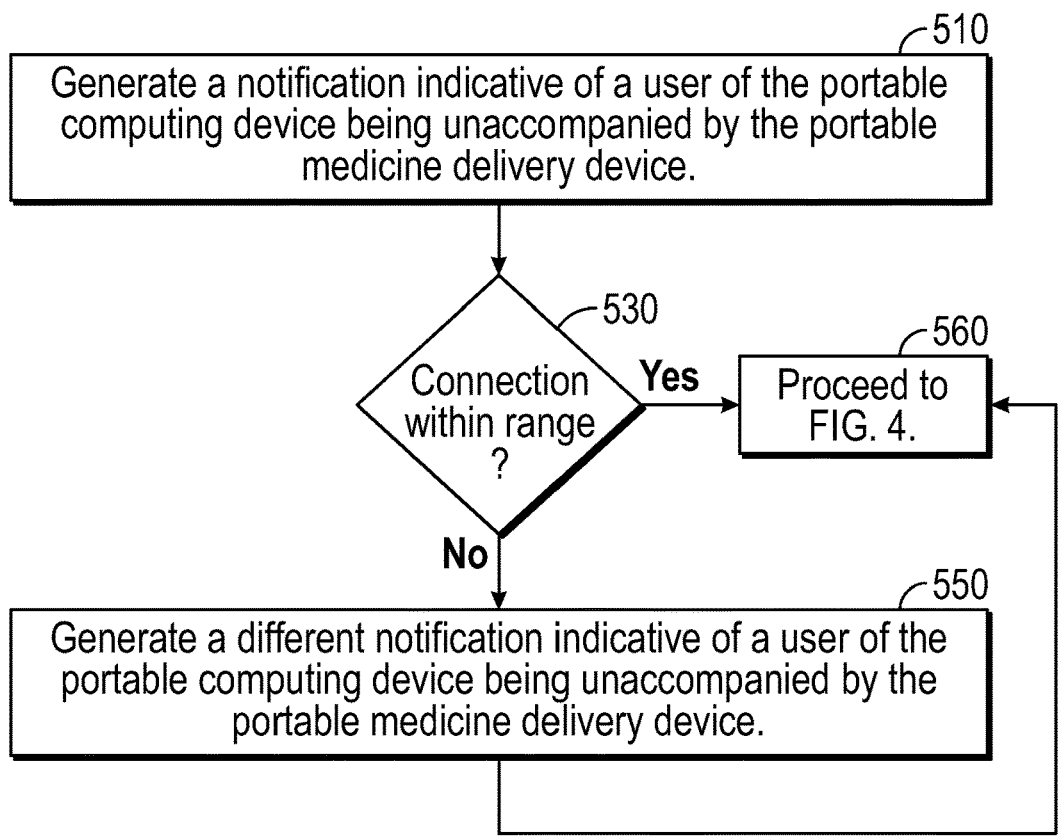

FIGS. 4-5 are flow diagrams depicting example techniques related to safeguards against separation from portable medicine delivery devices. Software (e.g., instructions corresponding to health management application 140) executing on a portable computing device (e.g., 130, FIG. 1) may cause performance of the techniques.

At block 410, a wireless connection established between a portable computing device and a portable medicine delivery device is monitored. For example, a health management application executing on the portable computing device may monitor a Bluetooth or Wi-Fi connection established between the portable computing device and the portable medicine delivery device. Monitoring the wireless connection may include obtaining (e.g., from an operating system of the portable computing device) data indicative of a connected state and/or a disconnected state of the wireless connection. Additionally or alternatively, monitoring the wireless connection may include obtaining (e.g., from an operating system of the portable computing device) data indicative of a strength of the wireless connection. Example data indicative of wireless connection strength include, but are not limited to, received signal strength indicator (RSSI) values for radio signals received at the portable computing device and/or at the portable medicine delivery device; and relative descriptors (e.g., "poor," "good," or "excellent") for radio signals received at the portable computing device and/or the portable medicine delivery device.

At block 430, a determination is made as to whether the portable medicine delivery device is within range, i.e., whether a communication connection with the portable medicine delivery device is still maintained and/or has at least a predetermined strength. For example, a health management application executing on the portable computing device may make this determination based on data (e.g., RSSI values) indicative of whether the portable medicine delivery device is inside or outside a predetermined range of the portable computing device.

The predetermined range may correspond to a maximum communication range for a particular wireless protocol. Thus, the portable medicine delivery device can be determined to be within the predetermined range based on detecting that a wireless connection is maintained between the portable medicine delivery device and the portable computing device. Conversely, the portable medicine delivery device can be determined to be outside the predetermined range based on detecting that a wireless connection is lost between the portable medicine delivery device and the portable computing device.

For example, the predetermined range may correspond to a maximum communication range of 30 feet for a Bluetooth connection. Accordingly, a portable medicine delivery device may be determined to be within 30 feet of a portable computing device if a Bluetooth connection is maintained between the portable medicine delivery device and the portable computing device. However, a portable medicine delivery device may be determined to be outside the predetermined range of 30 feet if a Bluetooth connection is lost between the portable medicine delivery device and the portable computing device.

Alternatively, the predetermined range may correspond to a distance that is correlated to a predetermined signal strength for a particular wireless protocol. Thus, the portable medicine delivery device can be determined to be inside the predetermined range based on detecting that an established wireless connection has at least the predetermined signal strength. Conversely, the portable medicine delivery device can be determined to be outside the predetermined range based on detecting that an established wireless connection has less than the predetermined signal strength. Detecting whether a wireless connection has at least the predetermined signal strength may involve obtaining a signal strength value for the wireless connection, comparing the signal strength value to a predetermined threshold value, determining that the wireless connection has at least the predetermined signal strength if the signal strength value is greater than or equal to the predetermined threshold value, and/or determining that the wireless connection has less than the predetermined signal strength if the signal strength value is less than the predetermined threshold value.

For example, the predetermined range may correspond to a distance of 3 feet, which may be correlated to a predetermined signal strength of −60 dBm for a Bluetooth connection. Accordingly, a portable medicine delivery device may be determined to be within 3 feet of a portable computing device if a Bluetooth connection has a RSSI value of at least −60 dBm. However, a portable medicine delivery device may be determined to be outside the predetermined range of 3 feet if a Bluetooth connection has a RSSI value that is less than −60 dBm. It should be appreciated that Bluetooth RSSI is merely provided as an example and that other technologies (e.g., Wi-Fi RSSI) can be used to determine signal strength.

Block 430 proceeds to optional block 440 if the portable medicine delivery device is within range. Otherwise, block 430 proceeds to block 500.

At optional block 440, a location record is stored (e.g., in memory 333 and/or data processing system 150). The location record indicates the location of the portable medicine delivery device. The location record may be generated based on obtaining and storing a timestamp and geolocation information. Depending on the hardware used in the portable medicine delivery device and the portable computing device, the geolocation information may include a GPS location, a location determined using cellular tower triangulation, a location determined using Wi-Fi positioning systems, and/or a location determined using another technology or technique. Additionally or alternatively, the location record may include user-provided location information (e.g., room descriptions such as "bedroom" or "kitchen") obtained via a user interface of the portable computing device.

At block 500, the example techniques depicted in FIG. 5 are performed. These example techniques are described in detail below.

The techniques of FIG. 4 are merely provided as examples, and variations are contemplated to be within the scope of the present disclosure. For example, in various embodiments, rather than establishing a communication connection with the portable medicine delivery device, the portable medicine delivery device may emit a predetermined signal, such as an RFID signal, among other things. The portable computing device may be equipped with a reader that can sense the predetermined signal, such as an RFID reader. The portable medicine delivery device and the portable computing device may be synchronized to, respectively, emit and sense the predetermined signal in the same time frame.

Referring to FIG. 5, at block 510, a notification is generated (e.g., by a health management application executing on the portable computing device). The notification may indicate that a user of the portable computing device not accompanied by the portable medicine delivery device. The notification may include any of a variety of messages, such as the message "Your insulin pen is out of reach" or the message "You are about to leave your insulin pen behind." The notification may include a visual message displayed on a screen, an audible message or indication, and/or a tactile impression (e.g., a vibration), among other things. The notification may be presented via a user interface of the portable computing device. For example, the notification may be an in-app notification, a notification presented in the notification center, and/or a notification displayed on the home screen of the portable computing device.

In some embodiments, the user may be provided with the last known location of the portable medicine delivery device. The last known location may be retrieved, for example, based on accessing the location record stored at optional block 440 of FIG. 4. The timestamp in the location record may be used to inform the user of the time when the portable medicine delivery device was tracked at the last known location. The last known location may be provided via the notification generated at block 510. Alternatively, the last known location may be provided via a separate notification.

In some embodiments, the user may be provided with information to assist the user with locating the portable medicine delivery device. For example, the information provided to assist the user may be travel directions for traveling to the last known location. To illustrate, the geo-location of the portable medicine delivery device may be plotted on a map of the environment (e.g., the user's home) to display visual information for navigating to the portable medicine delivery device. The information for assisting the user may be provided via the notification generated at block 510. Alternatively, this information may be provided separately from the notification (e.g., via a software application configured to execute on the portable computing device when a link included in the notification is clicked, tapped, or otherwise activated).

At optional block 530, a determination is made as to whether the portable medicine delivery device is within range. Optional block 530 may be similar to or different from block 430. In some embodiments, optional block 530 may be similar to block 430 in that the same predetermined range is used to make the determination. Thus, in some embodiments, at optional block 530, a determination is made as to whether the portable medicine delivery device is again within range. In some other embodiments, optional block 530 may be different from block 430 in that different predetermined ranges are used. The different predetermined ranges may correspond to the same wireless communication protocol (e.g., Bluetooth or Wi-Fi at both blocks) or different wireless communication protocols (e.g., Bluetooth at block 430 and Wi-Fi at block 530).

For example, the predetermined range used at block 430 may be 3 feet, whereas the predetermined range used at optional block 530 may be 30 feet. Thus, at block 430, a first determination can be made as to whether a Bluetooth connection has less than a predetermined strength, and at optional block 530, a second determination can be made as to whether a Bluetooth connection is lost.

Optional block 530 proceeds to optional block 550 if the portable medicine delivery device is not within range. Otherwise, optional block 530 proceeds to optional block 560.

At optional block 550, a different notification is generated (e.g., by a health management application executing on the portable computing device). The notification is indicative of a user of the portable computing device being unaccompanied by the portable medicine delivery device. However, this notification includes a message that is different from the message included in the notification generated at block 510. For example, if the notification of block 510 included the message "Your insulin pen is out of reach," the notification of optional block 550 may include the message "You are about to leave your insulin pen behind." Thus, the notification of block 510 and the notification of optional block 550 may include messages of differing granularity but may otherwise be similar.

At optional block 560, the example techniques depicted in FIG. 4 are performed. Thus, the example techniques of FIGS. 4-5 may be performed iteratively any number of times.

The techniques of FIG. 5 are merely provided as examples, and variations are contemplated to be within the scope of the present disclosure. For example, in various embodiments, the user may be queried about whether the portable medicine delivery device can be retrieved, and if the user responds that it is not possible to retrieve the portable medicine delivery device, information may be provided to assist the user with managing a health condition without the portable medicine delivery device. For example, carbohydrate intake recommendations may be provided if an insulin pen cannot be retrieved.

As mentioned above, the example techniques of FIGS. 4-5 relate to safeguards against separation from portable medicine delivery devices. Disclosed hereinafter are example techniques related to safeguards against usage of incorrect medicine delivery devices.

Although the example system of FIG. 1 is depicted with one portable medicine delivery device, it should be appreciated that systems including more than one portable medicine delivery device are also contemplated. For example, a person may use a first insulin pen to deliver fast-acting insulin and a second insulin pen to deliver long-acting insulin. However, having multiple portable medicine delivery devices can result in dangerous situations in which an incorrect device is used (e.g., the first pen is mistakenly used instead of the second pen or vice versa). Furthermore, such situations become more likely to occur when multiple portable medicine delivery devices have similar form factors.

Figure 6:
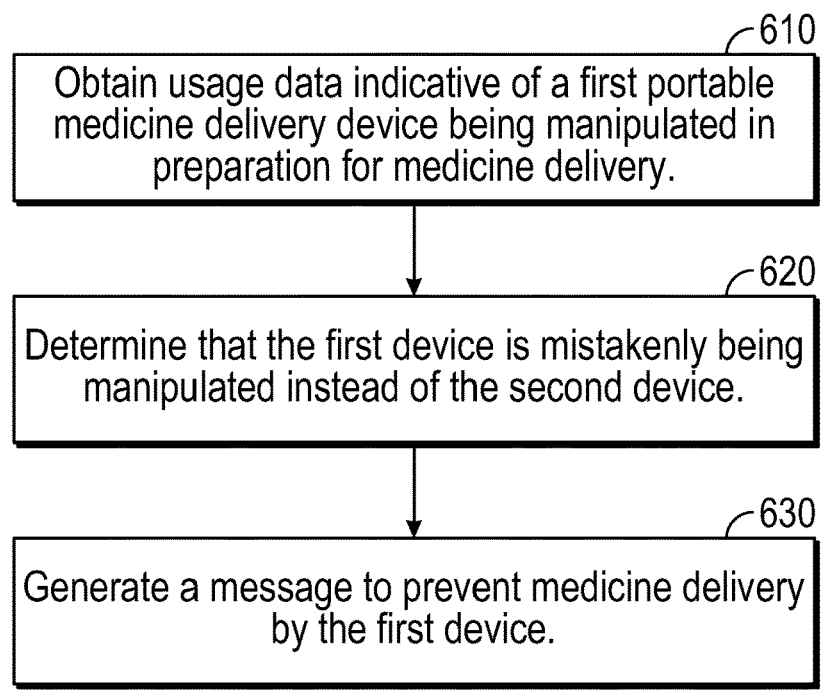
FIG. 6 is a flow diagram depicting example techniques related to safeguards against usage of incorrect medicine delivery devices, in accordance with aspects of the present disclosure.

In accordance with aspects of the present disclosure, such situations may be averted using various techniques (e.g., notifying a user that an incorrect device is about to be used and/or communicating a command to an incorrect device to prevent usage). Examples of such techniques are depicted in FIG. 6 and can be performed by software (e.g., instructions corresponding to health management application 140) executing on a portable computing device communicatively coupled to a plurality of portable medicine delivery devices. The plurality of portable medicine delivery devices may include a first device and a second device having similar form factors but configured to deliver different medicines. For example, the first device may be an insulin pen for delivering slow-acting insulin, and the second device may be an insulin pen for delivering fast-acting insulin.

Referring to FIG. 6, at block 610, usage data is obtained, and the usage data is indicative of the first device being manipulated in preparation for medicine delivery. Examples of the usage data include, but are not limited to, data indicative of the first device being manipulated to set a medicine delivery dose (e.g., via dose setting mechanism 228) and/or data indicative of an accelerometer (e.g., of electronics 227) detecting movement of the first device. The usage data may be communicated from the first device to the portable computing device (e.g., via a wireless connection).

At block 620, a determination is made that the first device is mistakenly being manipulated instead of the second device. As will be described in greater detail below, the determination can be made in various ways.

In some embodiments, making the determination may involve comparing the usage data against a recent therapy recommendation. For example, health management application 140 may generate a recommendation to take X units of fast-acting insulin, which is associated with the second device (e.g., via data stored in memory 333 that correlates the second device with fast-acting insulin). Thus, when the usage data is indicative of the first device being manipulated instead of the second device, a determination can be made that the first device is mistakenly being manipulated.

In some embodiments, making the determination may involve comparing the usage data against historical usage data of the first device and/or the second device. The comparison may be performed to determine whether the usage data is consistent with (e.g., similar to) the historical usage data of the first device or the second device. For example, the historical usage data of the first device may be analyzed to determine one or more time ranges (e.g., 7 to 9 a.m.) during which the first device was used in the past. The usage data obtained at block 610 may include time data that can be compared against the one or more time ranges to determine whether the time data fits within the one or more time ranges. If not, a determination can be made that the first device is mistakenly being manipulated.

The historical usage data of the first device and/or the second device may be accessed from one or more local and/or remote storage devices. For example, the historical usage data may be accessed from memory 333 and/or memory devices of a data processing system (e.g., 150, FIG. 1).

At block 630, a message is generated to prevent medicine delivery by the first device. Generation of the message may be responsive to determining that the first device is mistakenly being manipulated.

In various embodiments, the message may be a notification indicative of the first device being mistakenly manipulated. For example, the notification may include the reminder "Please confirm that the correct insulin pen is in use." The notification may be presented via a user interface of the portable computing device. For example, the notification may be an in-app notification, a notification presented in the notification center, and/or a notification displayed on the home screen of the portable computing device. The notification may include a visual message displayed on a screen, an audible message or indication, and/or tactile impression (e.g., vibration), among other things.

In various embodiments, the message may be a command that is communicated to the first device to disable a medicine delivery capability of the first device. For example, the command may electronically set a dosage to zero or may electronically trigger a locking mechanism that prevents delivery of medicine.

The various aspects, embodiments, and techniques described herein may be combined in various ways and/or performed in parallel and/or in sequence. In accordance with aspects of the present disclosure, the techniques disclosed in connection with FIGS. 4-6 involve data that may be analyzed to detect trends or patterns, which may be used to provide notifications, warnings, and/or recommendations to a user. For example, if data indicates that a person routinely leaves a portable medicine delivery device at a particular location or at a particular time, then that pattern of behavior may be used to provide notifications, warnings, and/or recommendations to the user; and if data indicates that a person routinely uses an incorrect portable medicine delivery device for a particular situation, then that pattern of behavior may be used to provide notifications, warnings, and/or recommendations to the user.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an aspect," "in aspects," "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

In one or more examples, the functional and/or operational aspects described herein may be implemented in hardware, software, firmware, or any combination thereof. If implemented in software, the functions may be stored as one or more instructions or code on a processor-readable medium and executed by a hardware-based processor. Processor-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more central processing units (CPUs), graphics processing units (GPUs), digital signal processors (DSPs), general purpose controllers or microcontrollers, general purpose microprocessors, application specific integrated circuits (ASICs), field programmable gate arrays (FPGAs), or other integrated or discrete logic circuitry capable of processing instructions. Accordingly, the term "processor" or "processing unit" as used herein may refer to any of the structures described herein or any other physical structure suitable for implementation of the techniques described herein. In some embodiments, the techniques could be fully implemented in one or more circuits or logic elements.

Any of the herein described operations, methods, programs, algorithms, or codes may be converted to, or expressed in, a programming language or computer program embodied on a computer, processor, or machine-readable medium. The terms "programming language" and "computer program," as used herein, each include any language used to specify instructions to a computer or processor, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted techniques. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system comprising:
   one or more processors; and
   one or more processor-readable storage media storing instructions which, when executed by the one or more processors, cause performance of:
   monitoring a wireless connection established between a portable computing device and a portable medicine delivery device;
   making a determination, based on a result of the monitoring, that the portable medicine delivery device is outside a predetermined range of the portable computing device; and
   based on the determination, generating a notification indicative of a user of the portable computing device being unaccompanied by the portable medicine delivery device.

2. The system of claim 1, wherein making the determination comprises detecting that the wireless connection is lost.

3. The system of claim 1, wherein making the determination comprises detecting that the wireless connection has less than a predetermined strength.

4. The system of claim 3, wherein detecting that the wireless connection has less than the predetermined strength comprises comparing a received signal strength indicator to a predetermined threshold value.

5. The system of claim 1, wherein the one or more processor-readable storage media further store instructions which, when executed by the one or more processors, cause performance of:
   prior to making the determination that the portable medicine delivery device is outside the predetermined range, determining that the portable medicine delivery device is within the predetermined range; and
   storing a location record indicating a location of the portable medicine delivery device.

6. The system of claim 5, wherein the one or more processor-readable storage media further store instructions which, when executed by the one or more processors, cause performance of:
   accessing the location record for the portable medicine delivery device; and
   providing the user with the location of the portable medicine delivery device indicated in the location record.

7. The system of claim 6, wherein providing the user with the location of the portable medicine delivery device comprises displaying visual information for navigating to the location of the portable medicine delivery device.

8. A processor-implemented method comprising:
   monitoring a wireless connection established between a portable computing device and a portable medicine delivery device;
   making a determination, based on a result of the monitoring, that the portable medicine delivery device is outside a predetermined range of the portable computing device; and
   based on the determination, generating a notification indicative of a user of the portable computing device being unaccompanied by the portable medicine delivery device.

9. The processor-implemented method of claim 8, wherein making the determination comprises detecting that the wireless connection is lost.

10. The processor-implemented method of claim 8, wherein making the determination comprises detecting that the wireless connection has less than a predetermined strength.

11. The processor-implemented method of claim 10, wherein detecting that the wireless connection has less than the predetermined strength comprises comparing a received signal strength indicator to a predetermined threshold value.

12. The processor-implemented method of claim 8, further comprising:
    prior to making the determination that the portable medicine delivery device is outside the predetermined range, determining that the portable medicine delivery device is within the predetermined range; and
    storing a location record indicating a location of the portable medicine delivery device.

13. The processor-implemented method of claim 12, further comprising:
    accessing the location record for the portable medicine delivery device; and
    providing the user with the location of the portable medicine delivery device indicated in the location record.

14. The processor-implemented method of claim 13, wherein providing the user with the location of the portable medicine delivery device comprises displaying visual information for navigating to the location of the portable medicine delivery device.

15. One or more non-transitory processor-readable storage media storing instructions which, when executed by one or more processors, cause performance of:
    monitoring a wireless connection established between a portable computing device and a portable medicine delivery device;
    making a determination, based on a result of the monitoring, that the portable medicine delivery device is outside a predetermined range of the portable computing device; and
    based on the determination, generating a notification indicative of a user of the portable computing device being unaccompanied by the portable medicine delivery device.

16. The one or more non-transitory processor-readable storage media of claim 15, wherein making the determination comprises detecting that the wireless connection is lost.

17. The one or more non-transitory processor-readable storage media of claim 15, wherein making the determination comprises detecting that the wireless connection has less than a predetermined strength.

18. The one or more non-transitory processor-readable storage media of claim 17, wherein detecting that the wireless connection has less than the predetermined strength comprises comparing a received signal strength indicator to a predetermined threshold value.

19. The one or more non-transitory processor-readable storage media of claim 15, wherein the one or more processor-readable storage media further store instructions which, when executed by the one or more processors, cause performance of:
  prior to making the determination that the portable medicine delivery device is outside the predetermined range, determining that the portable medicine delivery device is within the predetermined range; and
  storing a location record indicating a location of the portable medicine delivery device.

20. The one or more non-transitory processor-readable storage media of claim 19, wherein the one or more processor-readable storage media further store instructions which, when executed by the one or more processors, cause performance of:
  accessing the location record for the portable medicine delivery device; and
  providing the user with the location of the portable medicine delivery device indicated in the location record.

* * * * *